US006592552B1

(12) United States Patent
Schmidt

(10) Patent No.: US 6,592,552 B1
(45) Date of Patent: *Jul. 15, 2003

(54) DIRECT PERICARDIAL ACCESS DEVICE AND METHOD

(76) Inventor: Cecil C. Schmidt, 7400 Edinborough Way #5303, Edina, MN (US) 55435

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/933,858

(22) Filed: Sep. 19, 1997

(51) Int. Cl.[7] .............................................. A61M 5/178
(52) U.S. Cl. ........................ 604/164.01; 604/164.08; 604/164.09; 604/164.13; 604/176; 604/171; 606/185
(58) Field of Search ............................. 604/27, 35, 36, 604/43, 44, 48, 93, 117, 158, 161, 163, 164, 171, 173, 264, 272, 164.01, 164.08, 164.09, 164.13, 176; 606/181, 172, 185; 600/573, 576, 578, 583

(56) References Cited

U.S. PATENT DOCUMENTS

| | | | |
|---|---|---|---|
| 3,709,223 A | * 1/1973 | Macalalad et al. | 128/214.4 |
| 3,727,614 A | * 4/1973 | Kniazuk | 128/218 A |
| 3,923,060 A | 12/1975 | Ellinwood, Jr. | |
| 4,003,379 A | 1/1977 | Ellinwood, Jr. | |
| 4,052,989 A | * 10/1977 | Kline | 128/349 |
| 4,299,219 A | * 11/1981 | Norris, Jr. | 128/215 |
| 4,531,935 A | * 7/1985 | Berryessa | 604/45 |
| 4,668,226 A | * 5/1987 | Omata et al. | 604/272 |
| RE32,922 E | * 5/1989 | Levin et al. | 128/314 |
| 4,991,578 A | 2/1991 | Cohen | |
| 5,019,049 A | * 5/1991 | Haining | 604/165 |
| 5,071,412 A | 12/1991 | Noda | |
| 5,087,243 A | 2/1992 | Avitall | |
| 5,209,719 A | * 5/1993 | Baruch et al. | 604/22 |
| 5,213,570 A | 5/1993 | VanDeripe | |
| 5,220,917 A | 6/1993 | Cammilli et al. | |
| 5,269,326 A | 12/1993 | Verrier | |
| 5,336,252 A | 8/1994 | Cohen | |
| 5,356,416 A | * 10/1994 | Chu et al. | 606/140 |
| 5,368,047 A | * 11/1994 | Suzuki et al. | 128/765 |
| 5,387,419 A | 2/1995 | Levy et al. | |
| 5,524,757 A | * 6/1996 | Andrews et al. | 206/438 |
| 5,538,008 A | * 7/1996 | Crowe | 128/751 |

(List continued on next page.)

FOREIGN PATENT DOCUMENTS

| | | | |
|---|---|---|---|
| EP | 888 750 A1 | 1/1999 | |
| JP | 06258104 A1 | * 5/1996 | 600/437 |
| WO | WO 98/05289 | 2/1998 | |

OTHER PUBLICATIONS

Product Description Sheet by COMEDICUS Incorporated for A New Approach: Access The Pericardial Space With The PerDUCER™ Pericardial Access Device.
Medical Device & Diagnostic Industry, Advertisement, "SPECTRUM . . . precision from start to finish".
Advertisement "Corrosion–Resistant Alloys", Ulbrich Stainless Steels & Special Metals Inc.
Surgical Instruments, Advertisement for T.A.G. Medical Products Ltd.

*Primary Examiner*—Brian L. Casler
*Assistant Examiner*—Jennifer Maynard
(74) *Attorney, Agent, or Firm*—Beck & Tysver, P.L.L.C.

(57) ABSTRACT

The invention is directed to a device and method for minimally invasive access to the pericardial space of a human or animal patient. The disclosed pericardial access device includes a penetrating body axially mobile within the lumen of a guide tube. The distal end of the guide tube includes a shoulder to buttress pericardial tissue drawn into the guide tube by a suction force applied to the guide tube lumen. The penetrating body is subsequently distally advanced within the guide tube to access the pericardium.

5 Claims, 4 Drawing Sheets

U.S. PATENT DOCUMENTS

| | | | |
|---|---|---|---|
| 5,562,603 A | | 10/1996 | Moll et al. |
| 5,591,188 A | * | 1/1997 | Waisman .................... 606/182 |
| 5,630,802 A | * | 5/1997 | Moellmann et al. ........ 604/164 |
| 5,681,278 A | | 10/1997 | Igo et al. |
| 5,827,216 A | * | 10/1998 | Igo et al. ...................... 604/21 |
| 5,931,810 A | * | 8/1999 | Grabek ......................... 604/51 |
| 5,972,013 A | * | 10/1999 | Schmidt ...................... 606/185 |
| 6,063,039 A | * | 5/2000 | Cunningham et al. ....... 600/573 |
| 6,110,127 A | * | 8/2000 | Suzuki ........................ 600/565 |

\* cited by examiner

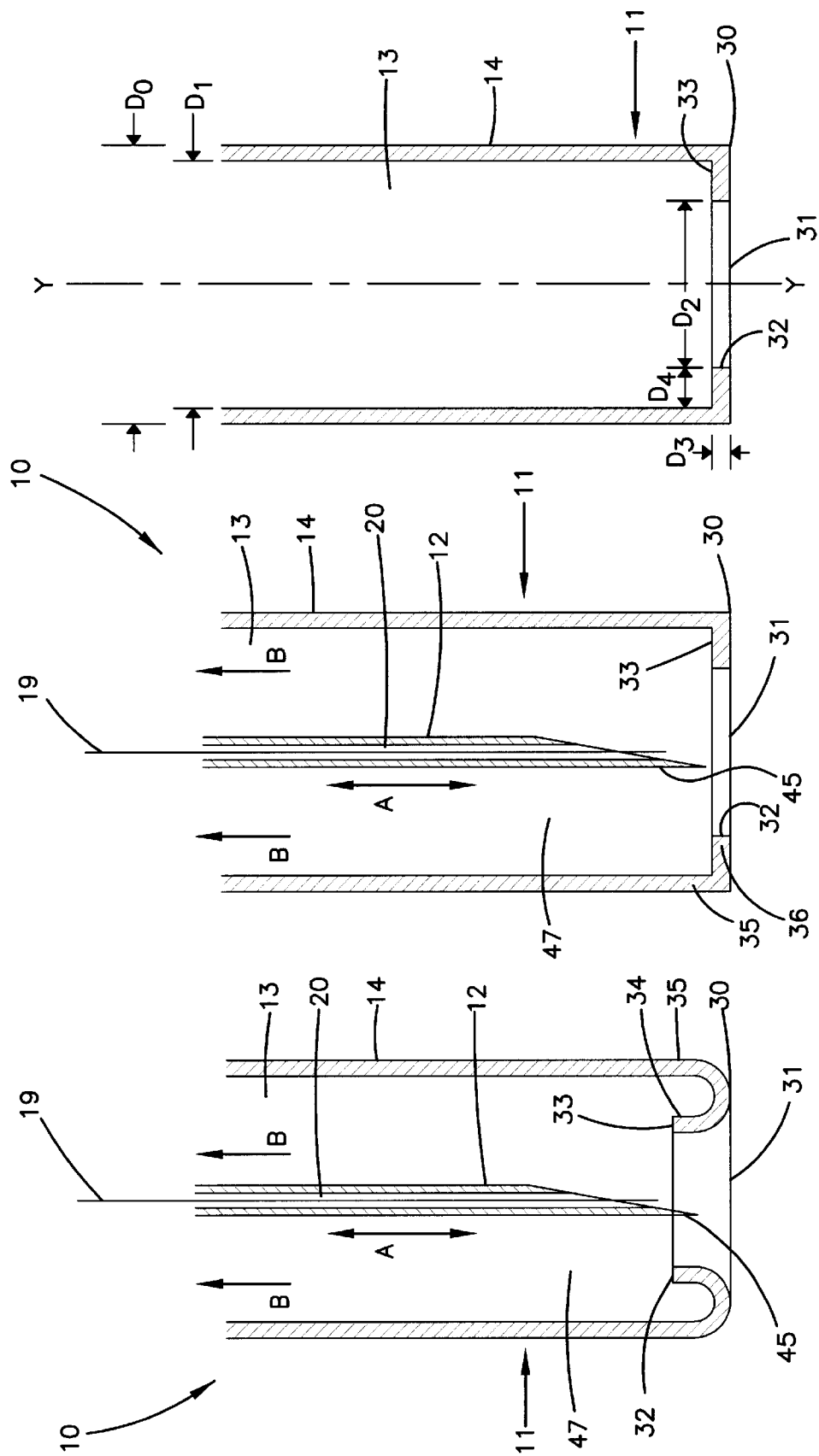

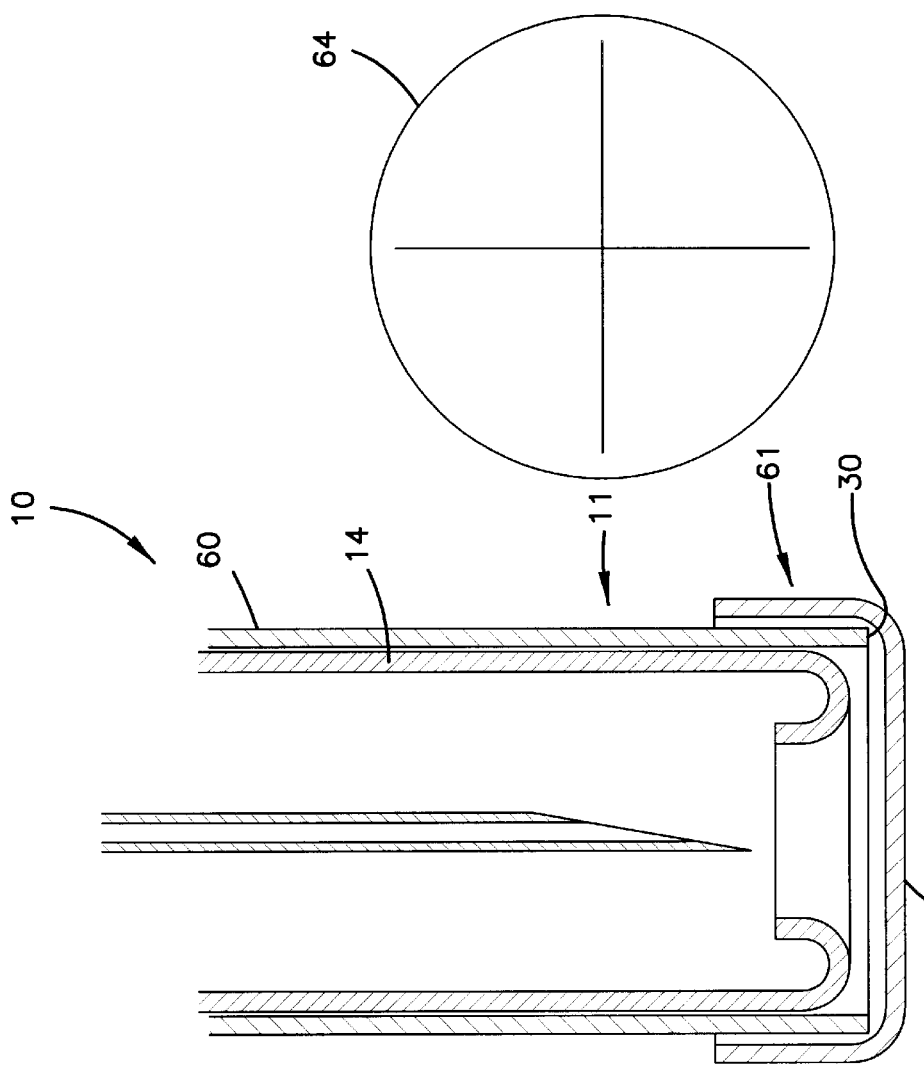
FIG. 9
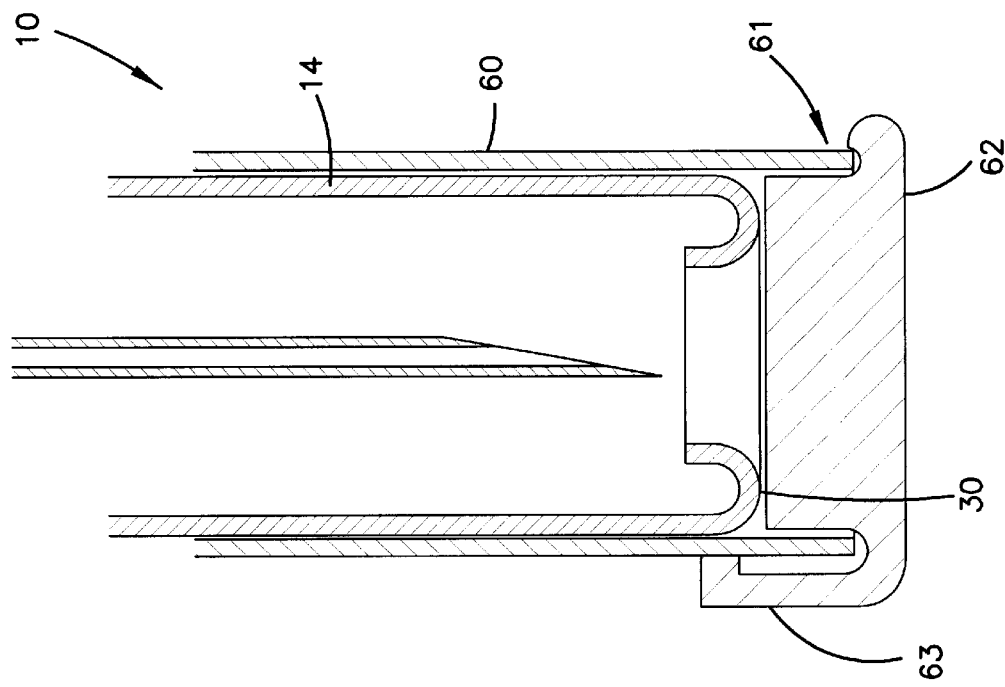
FIG. 8
FIG. 7

DIRECT PERICARDIAL ACCESS DEVICE AND METHOD

FIELD OF THE INVENTION

The present disclosure is directed to minimally invasive cardiac procedures. More specifically, the disclosure provides a device and method for accurate local access to the pericardial space with reduced risk of injury to the myocardium and associated coronary vessels.

BACKGROUND OF THE INVENTION

Knowledge of the pericardium (pericardial sac) dates back to the time of Galen (129–200 A.D.) the Greek physician and anatomist who created the term "pericardium." The pericardium (pericardial sac) is a conical membranous sac in which the heart and the commencement of the great vessels are contained. Gray's Anatomy (1977 ed.) pp. 457–460. The pericardium is fluid-filled and functions to prevent dilation of the chambers of the heart, lubricates the surfaces of the heart, and maintains the heart in a fixed geometric position. It also provides a barrier to the spread of infection from adjacent structures in the chest cavity and prevents surrounding tissue(s) from adhering to the heart. The space between the pericardium and the heart, known as the pericardial space, is normally small in volume and includes the fluid therein. It has been reported by others that when fluid is injected into the pericardial space it accumulates in the atrioventricular and interventricular grooves, but not over the ventricular surfaces. See, Shabetai R, "Pericardial and Cardiac Pressure," in *Circulation*, 77:1 (1988).

Pericardiocentesis, or puncture of the pericardium, heretofore has been performed for: 1) diagnosis of pericardial disease(s) by study of the pericardial fluid; 2) withdrawal of pericardial fluid for the treatment of acute cardiac tamponade; and 3) infusion of therapeutic agents for the treatment of malignant effusion or tumors. Thus, at present, intrapericardial injection of drugs is clinically limited to the treatment of abnormal pericardial conditions and diseases, such as malignant or loculated pericardial effusions and tumors. Drugs that have been injected into the pericardial space include antibiotic (sclerosing) agents, such as tetracycline and bleomycin or fibrinolytic agents such as streptokinase.

Intrapericardial drug delivery has not been clinically utilized for heart-specific treatments where pericardial pathology is normal, because the pericardial space is normally small and very difficult to access without invasive surgery or risk of cardiac injury by standard needle pericardiocentesis techniques. Normally, pericardiocentesis procedures are carried out by highly specialized, personnel in the cardiac catheterization laboratory of medical facilities, assisted by fluoroscopy and electrocardiogram monitoring equipment. Electrocardiographic monitoring of pericardiocentesis, using the pericardial needle as an electrode is commonly employed, as disclosed in Bishop L. H., et al., "The Electrocardiogram as a Safeguard in Pericardiocentesis," in *JMA*, 162:264 (1956), and Neill J. R., et al., "A Pericardiocentesis Electrode," in *The New England Journal of Medicine*, 264:711 (1961); Gotsman M. S., et al. "A Pericardiocentesis Electrode Needle," in *Br. Heart J.*, 28:566 (1966); and Kerber R. E., et al., "Electrocardiographic Indications of Atrial Puncture During Pericardiocentesis," in *The New England Journal of Medicine*, 282:1142 (1970). An echocardiographic transducer with a central lumen has also been used to guide the pericardiocentesis needle as reported in Goldberg B. B., et al., "Ultrasonically Guided Pericardiocentesis," in *Amer. J. Cardiol.*, 31:490 (1973).

However, there are complications associated with needle pericardiocentesis. These complications include laceration of a coronary artery or the right ventricle, perforation of the right atrium or ventricle, puncture of the stomach or colon, pneumothorax, arrhythmia, tamponade, hypertension, ventricular fibrillation, and death. Complication rates for needle pericardiocentesis are increased in situations where the pericardial space and fluid effusion volume is small (i.e., the pericardial size is more like normal and not abnormally distended by the accumulation of fluid, e.g., blood).

U.S. Pat. No. 5,071,428 (Chin et al.) discloses a method and apparatus for accessing the pericardial space for the insertion of implantable defibrillation leads. This method requires gripping the pericardium with a forceps device and cutting the pericardium with a scalpel (pericardiotomy) under direct vision through a subxiphoid surgical incision.

Uchida Y., et al., "Angiogenic Therapy of acute Myocardial Infarction by Intrapericardial Injection of Basic Fibroblast Growth Factor and Heparin Sulfate," in *Circulation AHA Abstracts* (1994), reported a method for the intrapericardial injection of angiogenic agents. While not described in detail, this method generally involved the percutaneous transcatheter bolus injection of drugs into the pericardial cavity via the right atrium. A major drawback of this method is that the right atrial wall is crossed, that could lead to bleeding into the pericardial space. In addition, the method involved the bolus injection of drugs rather than long-term.delivery via a catheter of controlled release material.

U.S. Pat. No. 4,991,578 (Cohen) discloses an apparatus for accessing the pericardial space for placement of defibrillation electrodes. The apparatus uses suction to "pull" the pericardium against a perforating needle housed in an outer catheter, thus impaling the pericardium on the needle (col. 15, lines 54–57). One of the stated problems with the apparatus is loss of suction. Col. 15, lines 4–5. A solution to the loss of suction proposed in the patent is to apply suction to pull the pericardium into the lumen of the catheter, apply a wire suture to stabilize the catheter tip and subsequently advance a piercing needle into the pericardium sutured to the catheter. In addition to other disadvantages the added step of suturing in this method is undesirable.

Another method for intrapericardial injection of agents is performed by a device, available under the name PerDUCER™ pericardial access device, available from Comedicus Incorporated, 3839 Central Avenue, NE, Columbia Heights, Minn. 55431. This device uses suction to create a lifted section of the pericardium, called a "bleb." Specifically, the bleb is secured to an elongate access device by a suction force exerted through a side wall port that is in a plane parallel to the longitudinal access of the device. Once formed, the bleb is punctured by a needle of limited travel that penetrates the bleb in a direction substantially tangential to the epicardial surface of the heart. While creating a bleb by suction through a side wall port combined with a tangential needle approach to the bleb can reduce the chance of puncturing or lacerating the myocardium, accurately penetrating the pericardium at a desired location may be difficult due to the motion of the heart during normal cardiac contraction relative to the orientation of the axial dimension of the a device.

Accordingly, there is a need for an accurate system for localized penetration of the pericardium which has low risk of causing penetration or laceration of the myocardium. Moreover, there is a need to effectively penetrate the pericardium without the chance of loss of vacuum and repeated attempts to effect penetration.

SUMMARY OF THE INVENTION

The present invention provides a device and method for safe access to the pericardial space without injury to the heart, in order to aspirate fluids directly from or to directly deliver fluids, i.e., therapeutic drugs, to the heart muscle or associated vasculature. With such safe access to the heart, complications from contacting the heart muscle are greatly reduced and nearly eliminated. Additionally, by directly delivering drugs to the heart muscle via the pericardium (pericardial sac), side affects associated with drug delivery by conventional administration methods, i.e., oral or injection, can be reduced, such that reduced dosages are needed to achieve the desired effect of a specific drug. Moreover, the present method for direct delivery of a drug provides for a wider range of drugs to be used.

A pericardial access device according to the invention includes a penetrating body that is axially mobile within the lumen of a guide tube. The guide tube has a proximal end for handling and operating the pericardial access device and a distal end having a distal port opening into the lumen of the guide tube. Within the distal end of the guide tube lumen there is an axially directed shoulder. The axially directed shoulder can be continuous around the circumference of the lumen or can be intermittent.

According to the invention, a suction or aspiration force is applied to the lumen of the guide tube to form a bleb of pericardial tissue in the distal lumen of the guide tube. That is, the suction draws the bleb of pericardium into the distal port such that it passes through the lumen opening between the axial shoulders and extends proximal thereto. A penetrating body having a piercing tip is axially mobile within the guide tube lumen. As the piercing tip of the penetrating body is advanced distally to pierce into the pericardial bleb, the bleb mushrooms outward forming edges which are buttressed by the shoulders. Thus, the shoulders prevent the bleb from moving away from the distal end of the guide tube and prevents breakage of the vacuum seal that maintains the bleb in a fixed location for accurate pericardial penetration. Subsequently, a guide wire can be passed through a lumen of the penetrating body, the pericardial access device removed and a material transport tube passed over the guide wire into the pericardial space for removal of fluid or delivery of materials therein.

At the proximal end of the pericardial access device, the handle region can include a vacuum inlet assembly for connecting an aspiration source to the device. In addition, the handle region can include a limiting mechanism for limiting the axial mobility of the penetrating body distally.

In some embodiments, a pericardial access device can include an exterior sheath having a reversibly sealed distal end to prevent fat, fascia, or other material from entering the distal end of the pericardial access device during placement.

The invention also provides a method for using a pericardial access device for accessing the pericardial space.

BRIEF DESCRIPTION OF THE DRAWINGS

FIG. 3 is a longitudinal section of a first embodiment of a distal end of a pericardial access device of the invention.

FIG. 4 is a longitudinal section of a second embodiment of a distal end of a pericardial access device of the invention.

FIG. 5 is a longitudinal section of the embodiment of FIG. 3 without penetrating body 3 and guidewire 10.

FIG. 7 is a longitudinal section of the distal end of a pericardial access device enclosed in a sheath with a reversibly sealed cap.

FIG. 8 is a longitudinal section of the distal end of a pericardial access device enclosed in a sheath with a reversibly sealed multi-flap hatch.

FIG. 9 is a distal end view of the reversibly sealed multi-flap hatch of FIG. 9.

DETAILED DESCRIPTION OF THE ILLUSTRATED EMBODIMENT

Figure 6:
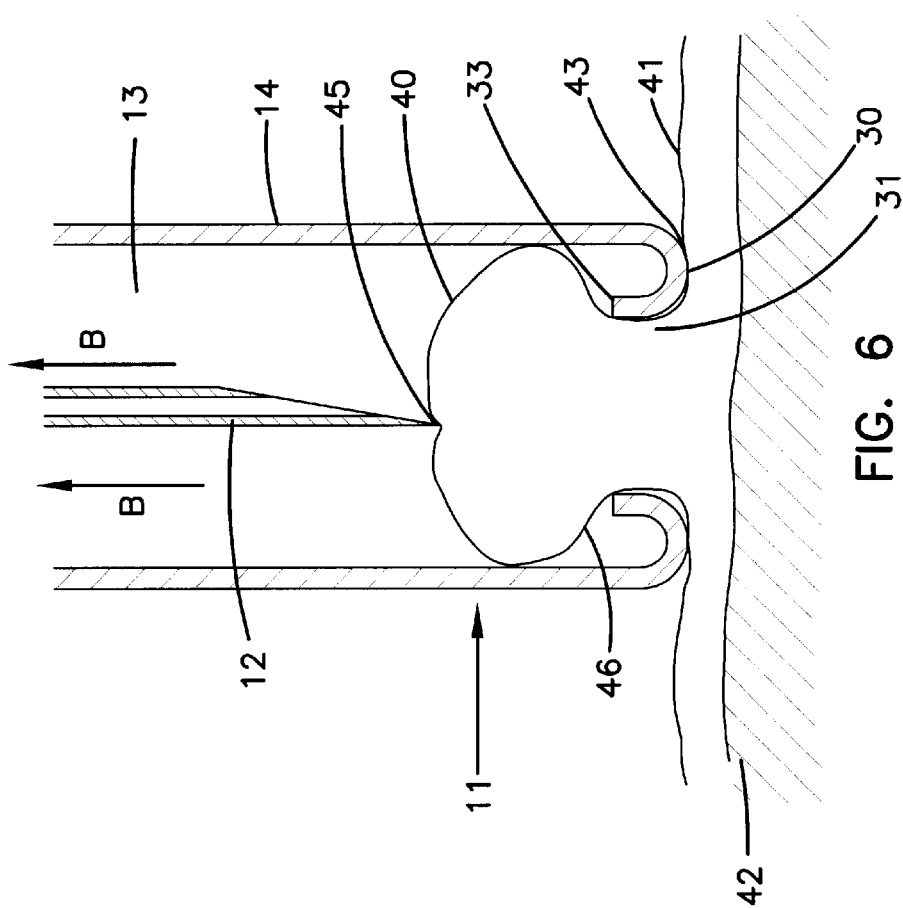
FIG. 6 is a longitudinal section of the distal end embodiment of the pericardial accesses device of FIG. 3 including a "bleb" of pericardium.

The invention will be described with reference to the accompanying drawings, wherein like reference numerals identify similar or corresponding components throughout the several views. The illustrated embodiments and description are for exemplary purposes to facilitate comprehension of the invention and should not be construed to limit the scope thereof. In addition, it will be noted that in several places throughout the specification, guidance is provided through lists of examples. In each instance, the recited list serves only as a representative group. It is not meant, however, that the list is exclusive.

A pericardial access device according to the present invention provides accurate local access to the pericardial space of a human or animal patient for introduction of a material therein, with a low risk of myocardial injury during access. Once the pericardial space is accessed, a material transport tube (e.g., a catheter) is inserted into the space for fluid withdrawal or delivery of a desired material.

As used herein, the term "material" refers to any material that can be introduced into the pericardial space through the material transport tube including gasses, liquids or solids. "Materials" include pharmaceutical agents such as vasodilators, antiplatelets, anticoagulants, thrombolytics, anti-inflammatories, antibiotics, fibrinolytics, antiarrhythmics, inotropics, antimitotics, angiogenics, antiatherogenic, etc. "Materials" also include heated or cooled fluids (e.g., ice water), flowable powders, controlled drug release implants, or other solid material that can pass through a material transport tube including, for example, implantable electrical leads.

Figure 1:
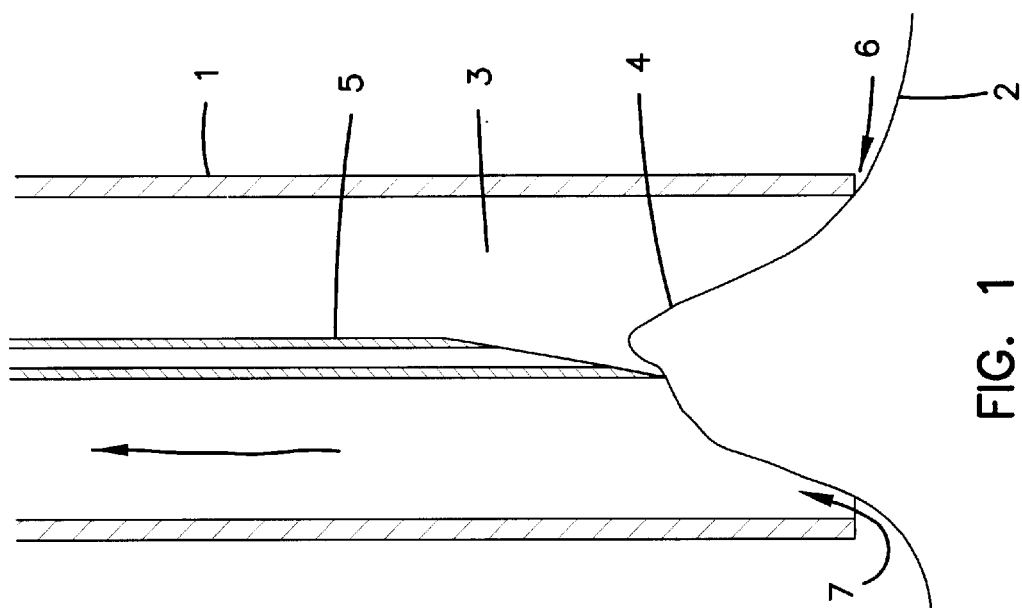
FIG. 1 is a longitudinal section of a distal end of a device for accessing the pericardial space that is outside the scope of the present invention.

One problem with some prior systems for accessing the pericardial space using suction is illustrated in FIG. 1. As shown, when tube 1 contacts the pericardium 2 and suction (arrows) is applied to lumen 3, bleb 4 is formed within the lumen 3. As a piercing instrument 5, such as a needle, is distally advanced to pierce bleb 4, the bleb 4 can be pushed away from the distal end 6 of the tube 1 allowing ambient air to rush in at, for example, arrow 7, thus breaking the vacuum seal which can result in tearing or non-penetration of the pericardium. The present invention overcomes the prior art problems by the herein disclosed distal end construction of the guide tube.

Figure 2:
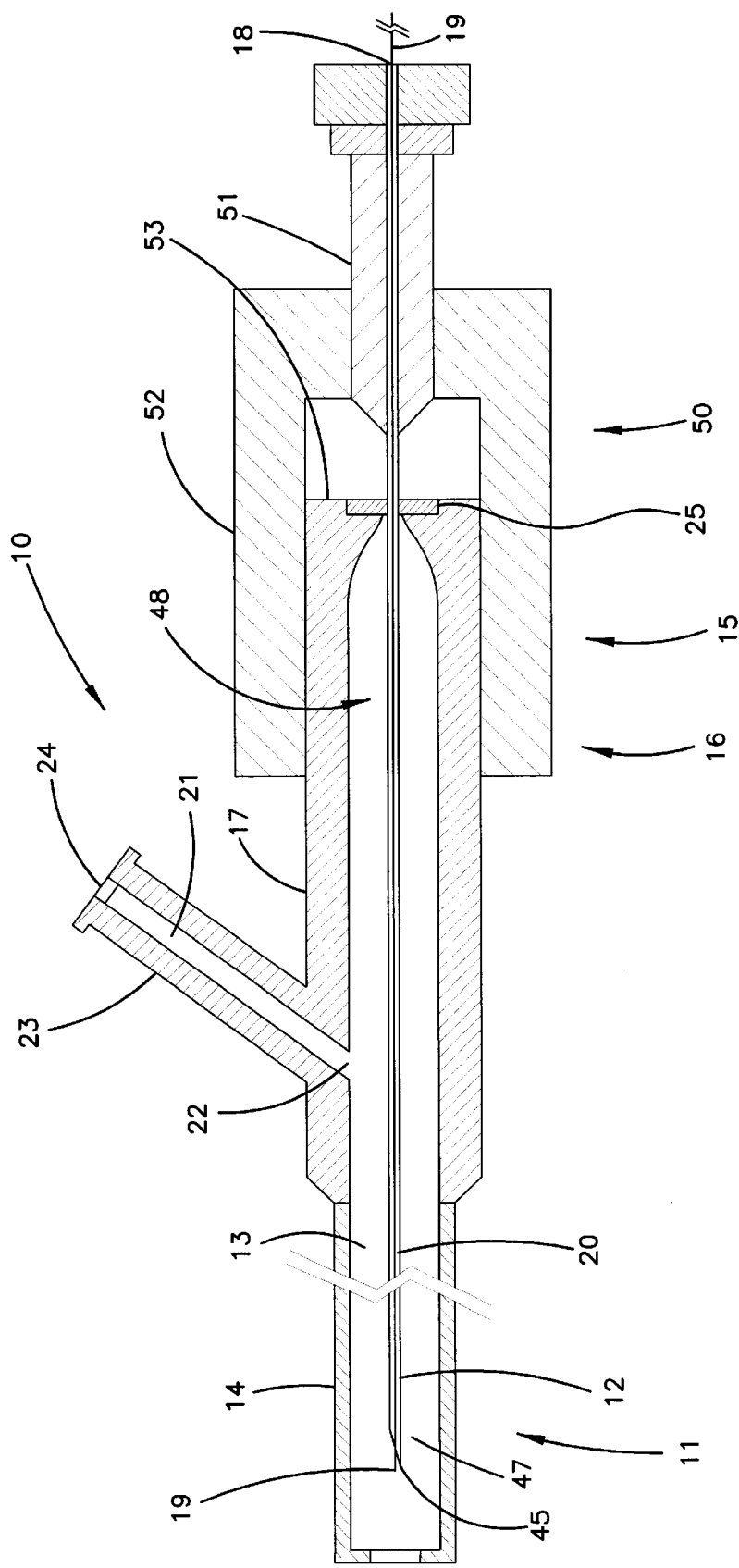
FIG. 2 is a longitudinal section of an embodiment of a pericardial access device of the invention.

Referring to FIG. 2, there is illustrated a longitudinal cross section view of one embodiment of a pericardial access device according to the invention. In this embodiment, the device 10 has a distal end 11 including a penetrating body 12 that is axially mobile within lumen 13 of guide tube 14. The device 10 has a proximal end 15 which includes a handle region 16 for holding and operating the device during use. The handle region 16 can include a vacuum inlet assembly 17 and a guide wire port 18 for passing a guide wire 19 through the lumen 20 of penetrating body 12. According to the invention, the vacuum inlet assembly 17 need not be located at the proximal end 15 but can be located anywhere that will permit a suction force to be applied to the distal end 11 of lumen 13 of guide tube 14.

The vacuum inlet assembly 17 includes a vacuum channel 21 having a distal end 22 that is in fluid communication with guide tube lumen 13. The proximal end 23 of the vacuum inlet assembly 17 includes a connector 24 such, as a luer lock for connecting a suction source (not shown) to the device 10. The device 10 also includes a sealing mechanism 25, such as a gasket, at a point proximal to the vacuum inlet channel 21 which, when a suction force is applied to the guide tube lumen 13, permits axial movement of penetrating body 12 without loss of suction, to the guide tube lumen 13, when the penetrating body 12 is moved.

FIGS. 3 and 4 are longitudinal section views of two different embodiments, of a distal end 11 of a pericardial access device 10 according to the invention. FIG. 5 is a longitudinal section view of the distal end 11 of guide tube 14 as illustrated in FIG. 4 without penetrating body 12 or guide wire 19.

Generally, a guide tube 14 of the invention can be prepared from plastic, stainless steel, titanium, ceramic or other material suitable for the herein below described function of a guide tube. At the distal end 11, guide tube 14 includes a distal tip 30 where guide tube lumen 13 opens to the exterior through a distal port 31. Thus, the distal port 31 is in a plane that is perpendicular to the longitudinal axis of guide tube 14 (Y—Y of FIG. 5). It will also be appreciated that the distal port 31 is in a plane that is perpendicular to both the direction of axial movement of penetrating body 12 (arrow A) and the direction of the suction force (arrow B) through guide tube lumen 13.

Referring to FIG. 5, the outside diameter $D_0$ of the guide tube 14 can be about 3 mm to 12 mm, typically about 6 mm to 8 mm. The diameter $D_1$ of the guide tube lumen 13 can be about 2 mm to 11 mm. At the distal end 11 of guide tube 14 near distal port 31, diameter $D_2$ of the guide tube lumen 13 is narrowed by an axial projection 32 or shoulder 33, that has a longitudinal dimension $D_3$ and an axial dimension $D_4$. The aspect ratio at the distal tip 30 of lumen 13 that results from dimensions $D_3$ and $D_4$ of shoulder 33 permits formation of the below described "bleb." As used herein, "aspect ratio" is the ratio of hole diameter to cylinder length (i.e., $D_2:D_3$). According to the invention, the hole diameter $D_2$ should be greater than the cylinder length, i.e., $D_2>D_3$. The aspect ratio is generally, at least 1:1, typically greater than about 2:1, preferably greater than 4:1.

Referring to FIG. 3, a shoulder 33 can be formed by rolling or folding the distal end 34 of the guide tube wall 35 into the guide tube lumen 13. Alternatively, referring to FIG. 4, the shoulder 33 can be an axial protrusion 36 from the guide tube wall 35 near the distal port 31. The shoulder 33 can be continuous around the circumference of the lumen 13 or intermittent. As used herein, "intermittent" refers to a shoulder 33 that has gaps around the circumference of the lumen but still functions as described below. It will be appreciated that other shoulder constructions that are not illustrated here but which provide the below described function are within the scope of the present invention.

Referring to FIG. 6 there is shown the embodiment of a shoulder 33 of FIG. 3 in use. According to the invention, aspiration is applied to create a suction force (arrow B) to the lumen 13 of guide tube 14 to form a bleb 40 of parietal pericardium 41 which surrounds the heart 42. As used herein, a "bleb" refers to the pericardial tissue which is drawn into the lumen 13 of guide tube 14 through distal port 31 when suction is applied to the lumen 13. Once formed, the bleb 40 is buttressed by shoulder 33 in a position that reduces the likelihood of the pericardium 41 moving away from distal tip 30 of guide tube 14 and breaking the point of the vacuum seal 43 when bleb 40 is contacted by the distally advancing piercing tip 45 of the below described penetrating body 12. As piercing tip 45 is advanced distally to pierce bleb 40, the bleb 40 can mushroom outward forming edges 46 which are buttressed by the guide tube shoulders 33 fixing the position of bleb during piercing. Fixing the bleb in place by the shoulders of the invention provides for atraumatic and accurate access to the pericardial space.

Referring now to FIG. 5, the longitudinal dimension $D_3$ of shoulder 33 can be about 0.25 mm to 5 mm, typically about 0.5 mm to 1.5 mm. The longitudinal dimension $D_3$ and axial dimensions $D_4$ of shoulder 33 determines the aspect ratio which should be selected based on considerations such as pericardial elasticity, pericardial size, pericardial thickness, amount of pericardial fluid, amount of suction force exerted, etc. The longitudinal dimension $D_3$, and axial dimension $D_4$, should be such that the bleb formed in guide tube lumen 13 is sufficiently buttressed to prevent loss of the vacuum seal 43 when the bleb is contacted by piercing tip 45. Therefore, in one embodiment a guide tube 14 can have an outside diameter $D_0$ of about 6 mm, a lumen diameter $D_1$ of about 4 mm, a continuous, or two or more intermittent shoulder(s) having an axial dimension $D_4$ of 0.75 mm, and a longitudinal shoulder dimension $D_3$ of about 0.5 mm creating a distal port diameter $D_2$ of about 2.5 mm and an aspect ratio of about 5:1.

Referring now to FIGS. 2–4, the penetrating body 12 is an elongate structure having a distal penetrating end 47 with a sharp piercing tip 45 for penetrating the pericardium. The penetrating body 12 has a proximal end 48 that extends to the handle region 16. An axial lumen 20, is present throughout the length of penetrating body 12, opens distally at penetrating end 47 and proximally at the guide wire port 18 to provide a channel for passing guide wire 19 through the access device 10 into the pericardial space. The outside diameter of the penetrating body 12 should provide for axial mobility within the guide tube lumen 13. The inside diameter of the guide tube lumen 20 should allow for passage of the guide wire 19. In a typical embodiment, the guide wire diameter can be about 0.2 mm to 0.8 mm.

The distal penetrating end 47 of the penetrating body 12, including the piercing tip 45, should be prepared from a material that can resist deformation when functioning to pierce the pericardium. Suitable materials include, for example, stainless steel, titanium, titanium alloys, etc. The proximal end 48 of the penetrating body 12 that extends to the handle region 16 can be a unitary structure having a lumen continuous with penetrating end 47. Alternatively, the penetrating body 12 can include one or more proximal segments (not shown) that have a lumen continuous with the lumen of the distal penetrating end 47. If proximal segments are used they can be prepared from any material which is sufficient to maintain a guidewire lumen and function to advance the piercing tip 45 into the pericardium, such as, plastic, stainless steel, titanium, titanium alloy, ceramic, etc.

In some embodiments, axial travel of penetrating body 12 within guide tube lumen 13 can be limited to prevent piercing tip 45 from traveling distally beyond the distal tip 30 of guide tube 14 which can result in penetration of the myocardium. Preferably, however, the distal travel of the penetrating body 12 is stopped before extending beyond the distal tip 30 of the guide tube 14. Referring to FIG. 2, in one embodiment, a limiting mechanism 50 can be located in the handle region 16 of the device 10. As shown in FIG. 2, the limiting mechanism 50 can include a collar 51 rigidly attached to the proximal end 48 of penetrating body 12. Distal travel of the penetrating body 12 is stopped when collar 51 contacts the proximal aspect 53 of vacuum inlet assembly 17. In the illustrated embodiment, the collar 51 is fixed to sleeve 52 which provides a grip for rotating or moving the penetrating body 12 axially. In alternative embodiments, a limiting mechanism can be located in the distal aspect of the guide tube to provide for limiting the axial travel of the penetrating body 12.

During use of a pericardial access device according to the invention, an incision of sufficient size for passage of the guide tube is made in the thoracic wall, for example in the subxiphoid region, using known methods. A second incision can be made for insertion of an endoscope into the thoracic cavity for visualization of the access procedure. Alternatively, the access procedure can be visualized with the aid of known external visualization systems, including, for example, fluoroscopy, ultrasound, etc. In a subxiphoid approach the device of the invention is advanced percutaneously through the first incision over the diaphragm into the mediastinal space until the distal end of the device contacts the pericardial surface of the heart. The device is aligned at a desired location on the pericardial surface of the heart and suction is applied to the guide tube lumen to form a bleb of pericardial tissue that passes into the guide tube lumen, through the distal port and extending proximal to the shoulders. Once the bleb is formed, the piercing tip of the penetrating body is advanced distally to pierce the bleb. A guidewire is then passed through the guidewire port through the lumen of the penetrating body and into the pericardial space. The device is removed and a catheter or other known material transport tube is guided over the guidewire into the pericardial space. The guide wire can be removed during fluid removal or administration of the desired material into the pericardial space. With a distal end of the material transport tube located in the pericardial space, a proximal end of the material transport tube can be fixed outside the patient's body, using known methods, for long or short term access to the pericardial space through the material transport tube.

A pericardial access device according to the invention can be advanced through the skin incision to the pericardial surface of the heart for accessing the pericardial space. Alternatively, an introducer or cannula can be passed through the skin incision to the pericardial surface and the pericardial access device passed through the introducer to the pericardial surface. Referring to FIGS. 7–9, in another embodiment, the pericardial access device 10 can be passed to the pericardial surface within an exterior sheath 60 having a reversibly sealed distal end 61. In the embodiment of FIG. 7, the distal end 61 of the exterior sheath 60 is reversibly sealed with a removable cap 62. The cap 62 is securely attached to the sheath 60 by a base 63. The removable cap 62 can be forced open by distal advancement of the device 10 within the sheath 60.

Alternatively, as shown in FIGS. 8 and 9, the distal end of sheath 61 can be reversibly sealed by a multi-flap hatch 64. Distal advancement of the access device 10 forces the multi-flap hatch 64 to open distally to allow exteriorization of the distal end 11 of the device 10. Therefore, according to this embodiment of the invention, the exterior sheath 60, including the pericardial access device 10, is passed through the skin incision to a position near, but not contacting, the pericardial surface. Once at the desired position, the guide tube 14 of the pericardial access device 10 is distally advanced to open the cap 62, or multi-flap hatch 64, allowing the distal tip 30 of guide tube 14 to contact the pericardial surface at the desired location for piercing the pericardium. Thus, the exterior sheath can fiction to prevent fat, fascia or other material from traveling retrograde into the lumen of the guide tube during placement.

It will be apparent to one of ordinary skill in the art that many changes and modifications can be made in the invention without departing from the spirit or scope of the appended claims.

I claim:
1. A pericardial access device comprising:
(a) a guide tube having a longitudinal axis, said guide tube having a lumen and including:
(i) a proximal end;
(ii) a distal end having a distal port opening communicating with said lumen, said distal port opening being in a plane which is substantially perpendicular to said longitudinal axis of said guide tube;
(iii) an axially directed shoulder in said lumen near said distal port, said shoulder is intermittent around a circumference of said lumen;
(b) a penetrating body axially mobile within said guide tube; a handle region mounted to said guide tube, said handle region including a vacuum inlet assembly whereby, an unconstrained bleb of tissue is formed proximate the opening by the application of vacuum to the vacuum inlet assembly.
2. A pericardial access device comprising:
(a) a guide tube having a longitudinal axis, said guide tube having a lumen and including:
(i) a proximal end;
(ii) a distal end having a distal port opening communicating with said lumen, said distal port opening being in a plane which is substantially perpendicular to said longitudinal axis of said guide tube;
(iii) an axially directed shoulder in said lumen near said distal port,
(b) a penetrating body axially mobile within said guide tube; a handle region mounted to said guide tube, said handle region including a vacuum inlet assembly whereby, an unconstrained bleb of tissue is formed proximate the opening by the application of vacuum to the vacuum inlet assembly;
(c) an exterior sheath surrounding said guide tube.
3. A pericardial access device comprising:
(a) a guide tube having a longitudinal axis, said guide tube having a lumen and including:
(i) a proximal end;
(ii) a distal end having a distal port opening communicating with said lumen, said distal port opening being in a plane which is substantially perpendicular to said longitudinal axis of said guide tube;
(iii) an axially directed shoulder in said lumen near said distal port,
(b) a penetrating body axially mobile within said guide tube, said penetrating body includes a lumen for passing a guide wire;
a handle region mounted to said guide tube, said handle region including a vacuum inlet assembly whereby, an unconstrained bleb of tissue is formed proximate the opening by the application of vacuum to the vacuum inlet assembly.

4. A pericardial access device comprising:
(a) a guide tube having a longitudinal axis, said guide tube having a lumen and including:
   (i) a proximal end;
   (ii) a distal end having a distal port opening communicating with said lumen, said distal port opening being in a plane which is substantially perpendicular to said longitudinal axis of said guide tube;
   (iii) an axially directed shoulder in said lumen near said distal port,
(b) a penetrating body axially mobile within said guide tube, said penetrating body includes a lumen for passing a guide wire;
a handle region mounted to said guide tube, said handle region including a vacuum inlet assembly whereby, an unconstrained bleb of tissue is formed proximate the opening by the application of vacuum to the vacuum inlet assembly;
guide wire positioned within said guidewire lumen.

5. A pericardial access device comprising:
(a) a guide tube having a longitudinal axis, said guide tube having a lumen and including:
   (iv) a proximal end;
   (v) a distal end having a distal port opening communicating with said lumen, said distal port opening being in a plane which is substantially perpendicular to said longitudinal axis of said guide tube;
   (vi) an axially directed shoulder in said lumen near said distal port,
(b) a penetrating body axially mobile within said guide tube;
a handle region mounted to said guide tube, said handle region including a vacuum inlet assembly whereby, an unconstrained bleb of tissue is formed proximate the opening by the application of vacuum to the vacuum inlet assembly;
a guide wire and a material transport tube positioned for pericardial access.

* * * * *